US00PP25024P2

(12) United States Plant Patent
Kolster

(10) Patent No.: US PP25,024 P2
(45) Date of Patent: Nov. 4, 2014

(54) ***PHOTINIA* PLANT NAMED 'KOLMAVOCA'**

(50) Latin Name: *Photinia×fraseri×Photinia serratifolia*
Varietal Denomination: Kolmavoca

(71) Applicant: Peter R. Kolster, Boskoop (NL)

(72) Inventor: Peter R. Kolster, Boskoop (NL)

(73) Assignee: Kolster Holding B.V., Boskoop (NL)

( * ) Notice: Subject to any disclaimer, the term of this patent is extended or adjusted under 35 U.S.C. 154(b) by 164 days.

(21) Appl. No.: 13/694,023

(22) Filed: Oct. 20, 2012

(51) Int. Cl.
*A01H 5/00* (2006.01)

(52) U.S. Cl.
USPC ..... Plt./226

(58) Field of Classification Search
CPC ..... A01H 5/0216; A01H 5/00
USPC ..... Plt./226
See application file for complete search history.

*Primary Examiner* — June Hwu
(74) *Attorney, Agent, or Firm* — C. A. Whealy

(57) ABSTRACT

A new and distinct cultivar of *Photinia* plant named 'Kolmavoca', characterized by its upright and outwardly spreading plant habit; relatively short internodes; glossy dark purplish brown-colored young leaves that become dark green with development; leaves with serrated and undulating margins; and tolerance to Powdery Mildew.

3 Drawing Sheets

Botanical designation: *Photinia×fraseri×Photinia Serratifolia.*

Cultivar denomination: 'KOLMAVOCA'.

BACKGROUND OF THE INVENTION

The present invention relates to a new and distinct cultivar of *Photinia* plant, botanically known as *Photinia×fraseri× Photinia serratifolia* and hereinafter referred to by the name 'Kolmavoca'.

The new *Photinia* plant is a product of a planned breeding program conducted by the Inventor in Boskoop, The Netherlands. The objective of the breeding program is to create new *Photinia* plants with intense red-colored developing leaves and tolerance to Powdery Mildew.

The new *Photinia* plant originated from a cross-pollination conducted by the Inventor in June, 2006 in Boskoop, The Netherlands of *Photinia×fraseri* 'Red Robin', not patented, as the female, or seed parent with an unidentified proprietary selection of *Photinia serratifolia*, not patented, as the male, or pollen, parent. The new *Photinia* plant was discovered and selected by the Inventor as a single plant within the progeny of the stated cross-pollination in a controlled greenhouse environment in Boskoop, The Netherlands in June, 2009.

Asexual reproduction of the new *Photinia* plant by vegetative cuttings in a controlled greenhouse environment in Boskoop, The Netherlands since June, 2009 has shown that the unique features of this new *Photinia* plant are stable and reproduced true to type in successive generations.

SUMMARY OF THE INVENTION

Plants of the new *Photinia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Kolmavoca'.

These characteristics in combination distinguish 'Kolmavoca' as a new and distinct *Photinia* plant:

1. Upright and outwardly spreading plant habit.
2. Relatively short internodes.
3. Glossy dark purplish brown-colored young leaves that become dark green with development.
4. Leaves with serrated and undulating margins.
5. Tolerance to Powdery Mildew.

Plants of the new *Photinia* differ primarily from plants of the female parent, 'Red Robin', in the following characteristics:

1. Leaves of plants of the new *Photinia* are smaller and darker in color than leaves of plants of 'Red Robin'.
2. Leaf margins of plants of the new *Photinia* are serrated and undulating whereas leaf margins of plants of 'Red Robin' are entire and non-undulating.
3. Plants of the new *Photinia* are more tolerant to Powdery Mildew than plants of 'Red Robin'.

Plants of the new *Photinia* differ primarily from plants of the male parent selection in the following characteristics:

1. Plants of the new *Photinia* are more compact and have shorter internodes than plants of the male parent selection.
2. Plants of the new *Photinia* have smaller leaves than plants of the male parent selection.

Plants of the new *Photinia* can be compared to plants of *Photinia hybrida* 'Kolcurl', disclosed in U.S. Plant Pat. No. 13,584. In side-by-side comparisons, plants of the new *Photinia* differed primarily from plants of 'Kolcurl' in the following characteristics:

1. Plants of the new *Photinia* had shorter internodes than plants of 'Kolcurl'.
2. Plants of the new *Photinia* had smaller leaves than plants of 'Kolcurl'.
3. Leaves of plants of the new *Photinia* were darker in color than leaves of plants of 'Kolcurl'.

BRIEF DESCRIPTION OF THE PHOTOGRAPHS

The accompanying colored photographs illustrate the unique appearance of the new *Photinia* plant showing the colors as true as it is reasonably possible to obtain in colored reproductions of this type. Colors in the photographs may differ from the color value cited in the detailed botanical description which accurately describe the colors of the new *Photinia* plant.

The photograph on the first sheet comprises a side perspective view of a typical plant of 'Kolmavoca' grown in a container.

The photograph on the second sheet is a close-up view of developing leaves of 'Kolmavoca'.

The photograph on the third is a close-up view of the upper surface of a typical fully expanded leaf of 'Kolmavoca'.

DETAILED BOTANICAL DESCRIPTION

Plants used in the aforementioned photographs and in the following description were grown during the summer and early autumn in three-liter containers in an outdoor nursery in Boskoop, The Netherlands and under cultural conditions which closely approximate commercial *Photinia* production. During the production of the plants, day temperatures ranged from 16° C. to 32° C. and night temperatures ranged from 8° C. to 18° C. Plants of the new *Photinia* were 15 months old when the photographs and description were taken. In the following description, color references are made to The Royal Horticultural Society Colour Chart, 2007 Edition, except where general terms of ordinary dictionary significance are used.

Botanical description: *Photinia×fraseri×Photinia serratifolia* 'Kolmavoca'.

Parentage:

*Female, or seed, parent.*—*Photinia×fraseri* 'Red Robin', not patented.

*Male, or pollen, parent.*—Unidentified proprietary selection of *Photinia serratifolia*, not patented.

Propagation:

*Method.*—By softwood cuttings.

*Time to initiate roots, summer.*—About 30 days at temperatures ranging from 18° C. to 30° C.

*Time to initiate roots, winter.*—About 45 days at temperatures ranging from 15° C. to 20° C.

*Time to produce a rooted young plant, summer.*—About 60 days at temperatures ranging from 18° C. to 30° C.

*Time to produce a rooted young plant, winter.*—About 100 days at temperatures ranging from 15° C. to 20° C.

*Root description.*—Fine, fibrous; cream in color.

*Rooting habit.*—Moderately freely branching; medium density.

Plant description:

*Plant and growth habit.*—Perennial shrub; upright and outwardly spreading plant habit; broad inverted triangle; strong stems; about ten lateral branches develop per plant, pinching enhances lateral branch development; moderately vigorous to vigorous growth habit.

*Plant height.*—About 42.7 cm.

*Plant diameter or area of spread.*—About 48.8 cm.

*Lateral branches.*—Length: About 20.9 cm. Diameter: About 3 mm. Internode length: About 2.5 cm. Texture: Smooth, glabrous. Strength: Strong. Color, developing: Close to 187B. Color, fully developed: Close to N199B.

Foliage description:

*Arrangement.*—Alternate, simple.

*Length.*—About 8.7 cm.

*Width.*—About 4.1 cm.

*Shape.*—Obovate.

*Apex.*—Apiculate.

*Base.*—Attenuate.

*Margin.*—Serrate; undulating.

*Texture, upper and lower surfaces.*—Smooth, glabrous.

*Luster, upper surface.*—Glossy.

*Luster, lower surface.*—Slightly glossy.

*Venation pattern.*—Pinnate.

*Color.*—Developing leaves, upper surface: Between 187A and darker than 200B. Developing leaves, lower surface: Between 182B and 183D. Fully expanded leaves, upper surface: Darker than between 139A and 147A; venation, close to 143A to 143B. Fully expanded leaves, lower surface: Close to 146B to 146C; venation, close to 144A.

*Petiole.*—Length: About 8 mm. Diameter: About 2 mm. Texture, upper and lower surfaces: Smooth, glabrous. Color, upper and lower surfaces: Close to 177A.

Flower description: Flower initiation and development have not been observed to date on plants of the new *Photinia.*

Disease & pest resistance: Plants of the new *Photinia* have been observed to be tolerant to Powdery Mildew. Plants of the new *Photinia* have not been observed to be resistant to pests or other pathogens common to *Photinia* plants.

Temperature tolerance: Plants of the new *Photinia* have been shown to be tolerant to temperatures ranging from about −15° C. to about 45° C.

It is claimed:

1. A new and distinct *Photinia* plant named 'Kolmavoca' as illustrated and described.

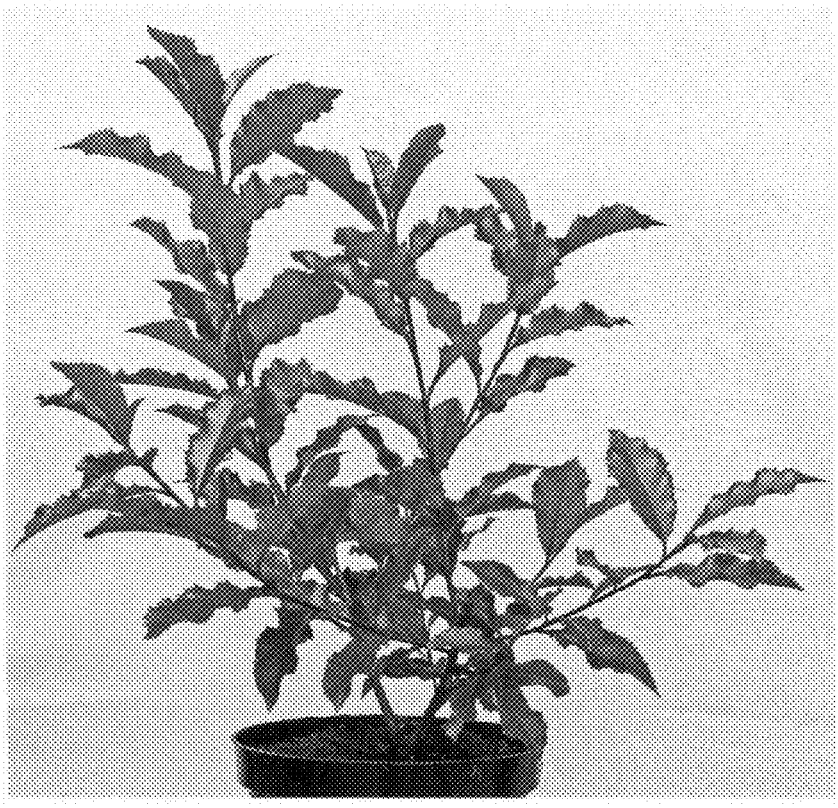

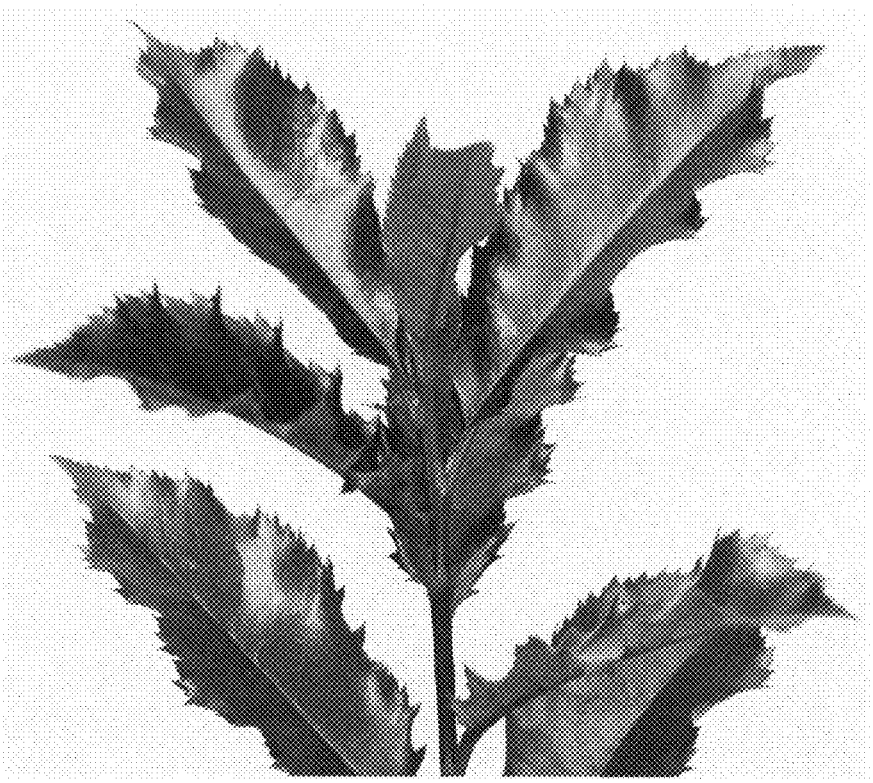

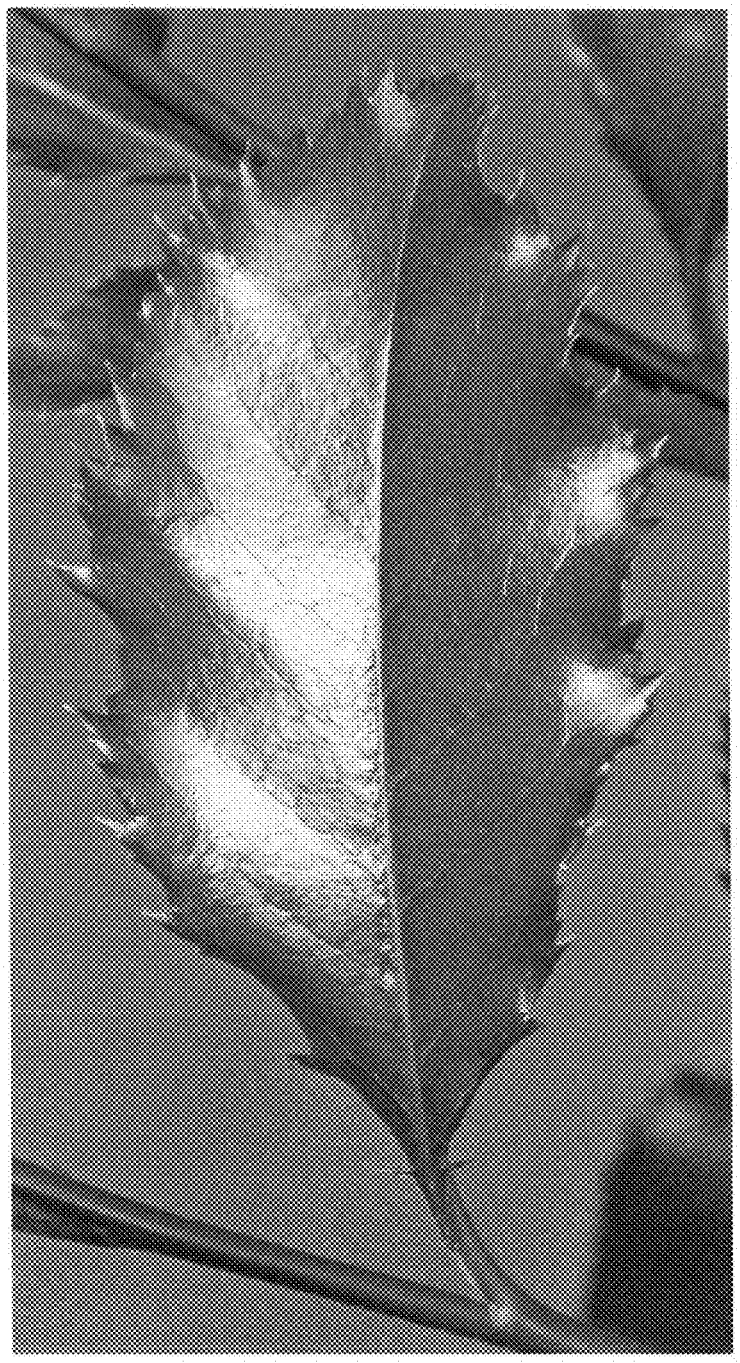

* * * * *